United States Patent [19]

Berlin et al.

[11] Patent Number: 4,484,911
[45] Date of Patent: Nov. 27, 1984

[54] CANNULA AND CLAMP DEVICE

[76] Inventors: Richard B. Berlin, 309 Engle St.;
Stephen L. Javna, 163 Engle St.;
Richard B. Berlin, Jr., 309 Engle St.,
all of Englewood, N.J. 07631

[21] Appl. No.: 428,138

[22] Filed: Sep. 29, 1982

[51] Int. Cl.³ .............................................. A61B 17/00
[52] U.S. Cl. .......................... 604/174; 128/DIG. 12; 128/346
[58] Field of Search ................ 604/174, 180; 128/321, 128/322, 346, DIG. 12; 27/24 A

[56] References Cited

U.S. PATENT DOCUMENTS

| | | | |
|---|---|---|---|
| 611,038 | 9/1898 | Lohman | 27/24 A |
| 2,234,686 | 3/1941 | Walter | 604/174 X |
| 2,662,524 | 12/1953 | Hudgins | 604/174 |
| 3,241,476 | 3/1966 | Vogt | 604/174 X |
| 3,814,080 | 6/1974 | Norman | 604/174 X |

Primary Examiner—Stephen C. Pellegrino
Attorney, Agent, or Firm—Depaoli & O'Brien

[57] ABSTRACT

This invention provides a cannula-clamp device which is adapted for operative cystic cholangiography. In a preferred embodiment, the jaw members and extended shafts of the device are constructed of radiolucent material such as plastic.

12 Claims, 11 Drawing Figures

CANNULA AND CLAMP DEVICE

BACKGROUND OF THE INVENTION

Operative cholangiography has been undergoing an evolution since Mirizzi first advocated the routine use of operative cholangiography in Surg. Gynecol. Obstet., 65, 702 (1937). A variety of cannulas, clamps and catheters have been recommended for this purpose. Since the techniques to fasten the cannula to the cystic duct involve cumbersome manipulation, and frequently allow dye leakage or bubble injection, surgeons have been reluctant to employ this intraoperative diagnostic modality routinely during biliary surgery.

The objective in operative cholangiography is to inject radiopaque dye into the cystic duct of the gall bladder so that it passes into the common bile duct to opacify it to x-rays to facilitate detection of stones, tumors, strictures, anomalies and the like, during biliary surgery. The operative cavity is 10–15 centimeters in depth and it is difficult and time-consuming to effect a tie around the cystic duct to contain and seal a catheter for injection of dye.

The characteristics of an ideal cannula for operative cholangiography should satisfy such criteria as (1) insertion should be readily achieved; (2) the mechanics should not obscure vision during cannulization; (3) the method of securing the cannula should not be cumbersome or time-consuming; (4) there should be no significant resistance to flow of dye during injection; (5) connections should not leak; (6) surrounding delicate vital structures should not be endangered; and (7) no opaque foreign material should appear on the x-rays other than dye.

In Am. J. Surg., 123, 741 (1972) there is reported the use of a Fr. 5 Lehman radiopaque catheter fixed in position with a hemoclip. Such clips may interfere with future diagnostic modalities such as computerized radiographic or electro-magnetic tomography. More recent efforts to advance techniques and provide improved cannula and clamp devices for operative cholangiography are described in Arch. Surg., 111, 608 (1976); Arch. Surg., 112, 340 (1977); Arch. Surg., 113, 729 (1978); Arch. Surg., 114, 749 (1979); Arch. Surg., 115, 229 (1980); Am. J. Surg., 137, 826 (1979); JAMA, 246(4), 380 (1981); Medical Radiography and Photography, 57(1), 18 (1981); and references cited therein.

Several hundred thousand patients undergo biliary surgery annually in the United States. Many experienced surgeons agree that cholangiography should be performed routinely. There remains a need for improved means for operative cholangiography.

Accordingly, it is an object of the present invention to provide a novel surgical device which is adapted for cholangiography.

It is another object of this invention to provide a cannula and clamp device for operative cholangiography which is constructed substantially of radiolucent material.

It is a further object of this invention to provide a cannula and clamp device for operative cholangiography which can be applied and removed rapidly with single hand manipulation.

Other objects and advantages of the present invention shall become apparent from the accompanying description and drawings. Applications for angiography are contemplated with modified version of the same invention.

U.S. Pat. Nos. of general interest with respect to the present invention include 611,038 (1898); 2,234,686; 3,019,790; 3,166,819; 3,500,820; and 3,814,080.

SUMMARY OF THE INVENTION

One or more objects of the present invention are accomplished by the provision of a cannula and clamp device adapted for operative cystic duct cholangiography comprising (1) a first jaw member with an extended shaft; (2) a second jaw member which is coextensive and movably connected to said first jaw member wherein the gripping ends of the jaw members in contacting proximity form an annular open-ended cross-section; (3) biasing means for urging said jaw members into contacting proximity; and (4) a cannula which is attached to and inwardly supported by the first jaw member, wherein the injection end of the cannula is positioned and centered in the annular cross-section formed by the gripping ends of the jaw members, and the feed end of the cannula extends rearwardly and outwardly from the first jaw member. The jaws are designed to seal tightly around various sizes of ducts.

In a particularly preferred embodiment of the cannula and clamp device, the jaw members and extended shafts are constructed of radiolucent material.

DETAILED DESCRIPTION OF INVENTION EMBODIMENTS

A present invention cannula and clamp device, for purposes of intraoperative cholangiography, can vary in length dimension in a range between about 5–20 centimeters. The annular open-ended cross-section of the closed jaw members must be of suitable diameter to encompass the combined annular cross-section of the cystic duct and inserted cannula injection end, e.g., an open-ended diameter of about 2–6 millimeters.

The annular open-ended cross-section of the jaw members in contacting proximity can be either circular or non-circular. An important consideration is the accommodation of cystic duct stumps of different diameters and tissue textures, and concomitantly the achievement of a gripping seal between the cystic duct stump and the inserted cannula end.

Figure 4A:
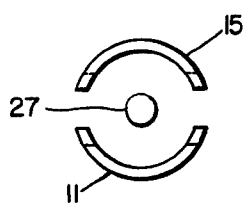
FIG. 4–FIG. 7 are side and front elevations of various gripping end configurations and the jaw members of a present invention cannula and clamp device.
Figure 4B:
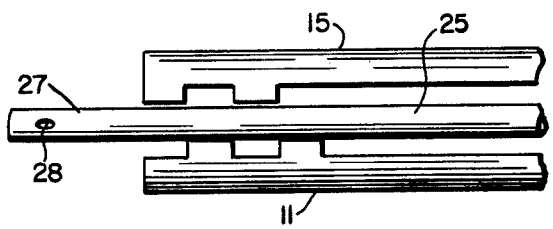

In FIG. 4, the gripping ends of the jaw members are matching incomplete semi-circles relative to the open-ended cross-section that they form.

Figure 5A:
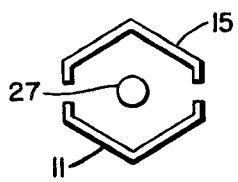
Figure 5B:
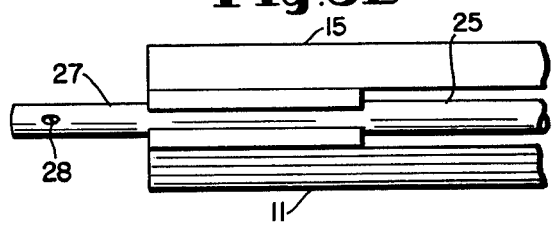

In FIG. 5, the gripping ends of the jaw members are matching non-circular structures relative to the open-ended cross-section that they form.

Figure 6A:
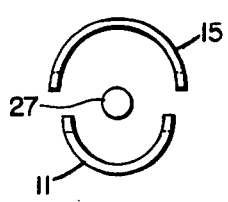
Figure 6B:
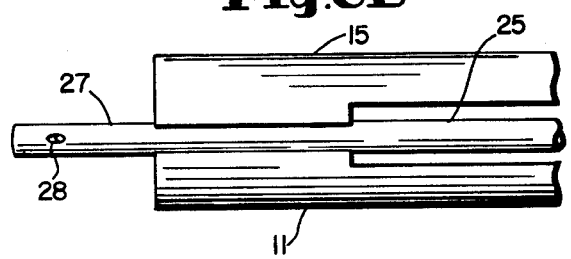

In FIG. 6, the gripping ends of the jaw members are non-matching semi-circular arcs which close in an overlapping configuration relative to the open-ended cross-section that they form.

Figure 7A:
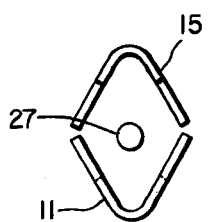
Figure 7B:
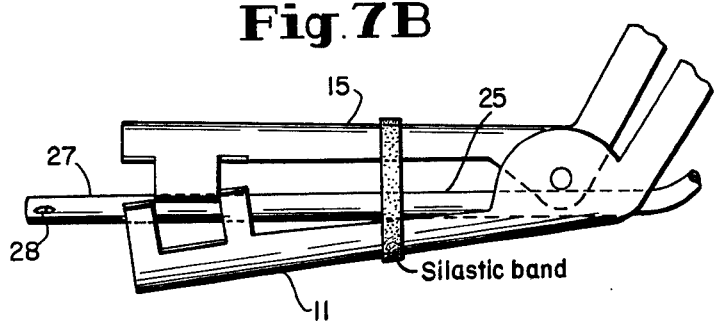

In FIG. 7, the gripping ends of the jaw members are inverted matching structures which close in an overlapping teeth paraboloid configuration relative to the open-ended cross-section that they form.

A present invention cannula and clamp device can be fabricated with either metal and/or plastic structural components. The device is designed for easy disassembly to facilitate cleaning and sterilizing. In another embodiment, low cost disposable cannula and clamp devices are contemplated, e.g., surgical devices produced with inexpensive molded plastic or cellulosic components.

A further embodiment of the present invention relative to operative cholangiography is the use of radiolucent components in the construction of the cannula and clamp device. Illustrative of radiolucent materials are plastics such as polypropylene, polycarbonate, fiber-reinforced polyethylene or polystyrene, and the like.

The radiolucent construction of the major clamp components prevents interference with the cholangiographic x-ray identification of unsuspected biliary calculi or strictures.

The cannula component need not be radiolucent, and can be in the form of a smooth blunt tip metal tube (either closed or open-ended) which is suitably perforated near the blunt injection tip. The outside diameter of the cannula tube usually will be about 1.5–2.0 millimeters.

The liquid-discharge perforations preferably are located along the barrel of the cannula as well as at the tip. This type of structure minimizes clogging of the perforations during insertion of the cannula tip into a cystic duct stump, and avoids a jet stream effect which tends to back-pressure the cannula out of the cystic duct stump.

The elongated cannula body preferably is longitudinally rigid and laterally flexible. The lateral flexibility permits the injection end of the cannula to be deflected and manipulated in order to accommodate a thick-walled cystic duct stump. The cannula can be constructed of steel, or of a plastic such as polypropylene or high density polyethylene which are readily shaped into semi-rigid conduits.

The feed end of the cannula is attached to a flexible plastic tubing through which a fluid contrast medium is supplied under mild hydrostatic pressure. Illustrative of a contrast media are 25% Hypaque solution (Winthrop Laboratories), Conroy 30% diluted (Diagnostic Products) and Reno-M-60 (Squibb and Sons). Before insertion of the injection end of the cannula into a cystic duct stump, or into a small incision in a cystic duct, the cannula and attached feed system is rinsed and liquid-filled to exclude bubbles.

Figure 1:
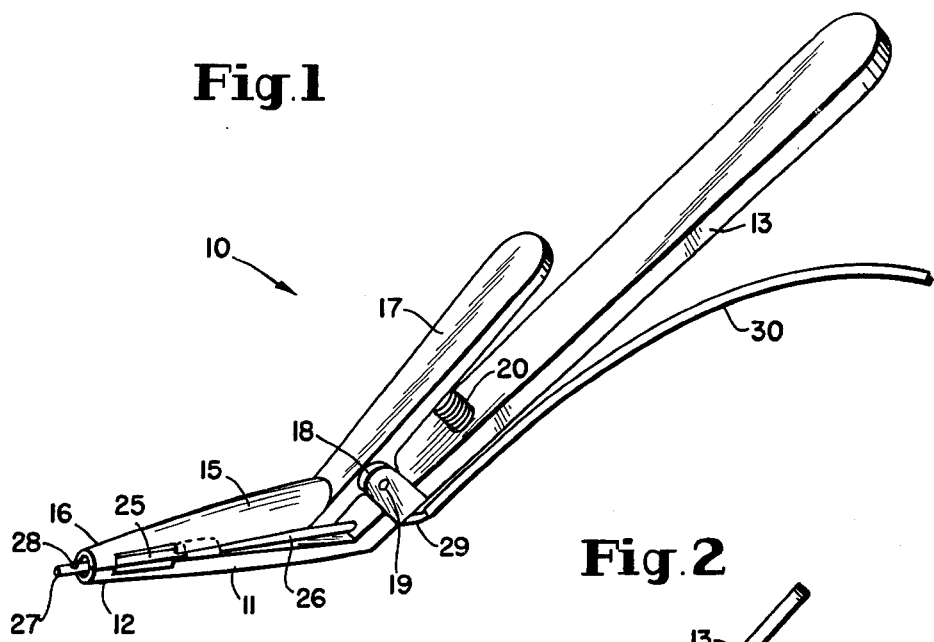
FIG. 1 is a perspective view of a preferred embodiment of a present invention cannula and clamp device with the jaw members and the extended shafts angled in a nonlinear configuration.
Figure 2:
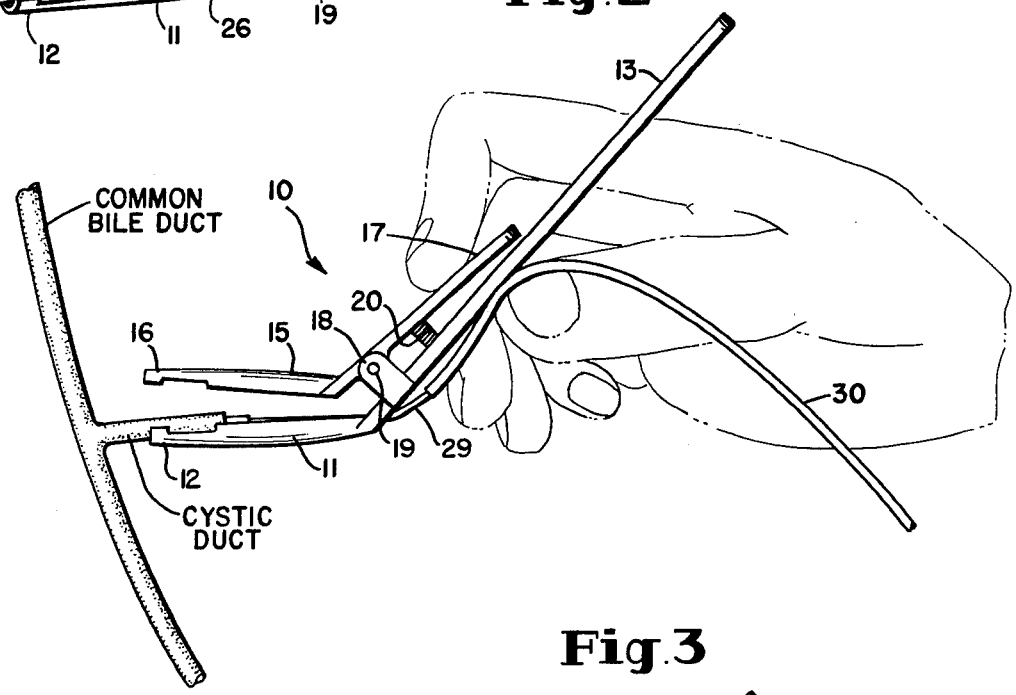
FIG. 2 is a side elevation of the same cannula and clamp device being hand operated for insertion of the rigid cannula injection end into a cystic duct stump.
Figure 3:
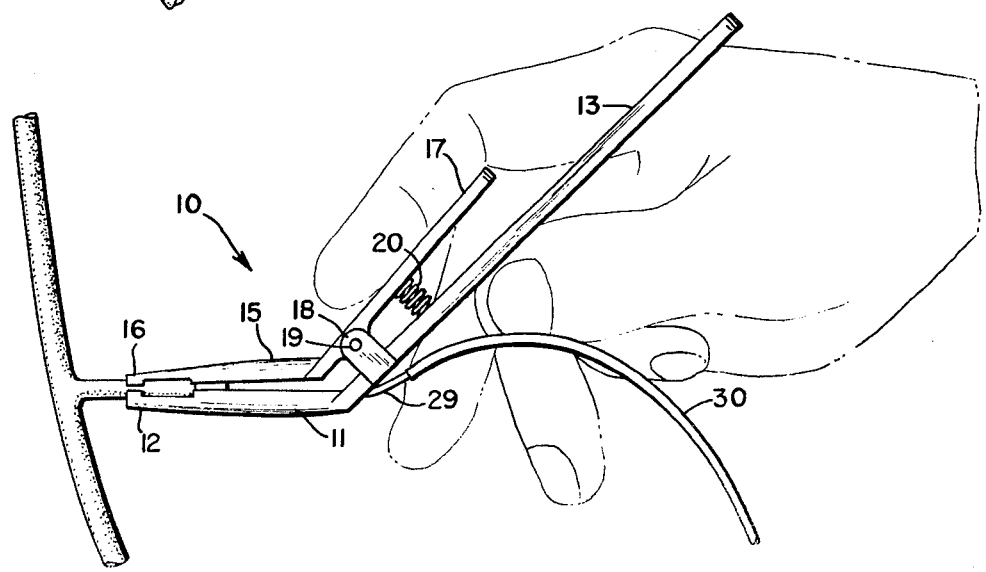
FIG. 3 is a side elevation of the FIG. 2 cannula and clamp device after hand operated release of the spring-controlled jaw member to close the clamp and effect a gripping seal between the cystic duct stump and the cannula end, prior to injection of a fluid dye medium. Instead of a spring type of bias means, an elastic band may be employed to encircle and close the jaw members as shown in FIG. 7.

In FIG. 1, a cannula-clamp device 10 for operative cholangiography is illustrated which is constructed of molded plastic components, with the exception that the cannula and coil spring are composed of metal. The injection end of the perforated cannula is centered in the annular cross-section and extends beyond the gripping ends of the jaw members. The extended shaft of the movable second jaw member is shorter than that of the first jaw member. The curbed configuration of the cannula-clamp device facilitates palming for one-handed manipulation.

Cannula-clamp device 10 as represented has a first jaw member 11, which has a gripping end 12 and an extended shaft 13.

The second jaw member 15 has a gripping end 16 and an extended shaft 17. Second jaw member 15 is movably connected between a pair of support arms 18 extending vertically from shaft 13, and second jaw member 15 can be movably rotated in a short arc clockwise and counterclockwise about pivot point 19 to open and close gripping ends 12 and 16 of the first and second jaw members.

Coil spring 20 maintains the jaw members in a closed position, until hand-pressure is applied to the extended shafts 13 and 17 to counteract the coil spring 20 bias. As noted previously an elastic band can be employed as the bias means, located between the gripping ends and the pivot point of the two jaw members.

Cannula tube 25 is supportedly integrated with first jaw member 11 at position 26. The injection end 27 of cannula tube 25 has perforations 28 for emission of a dye solution under hydrostatic pressure. The feed end 29 of cannula tube 25 is attached to a flexible tubing 30, which in turn is connected to a dye solution reservoir, e.g., a large capacity syringe.

Various cannula and clamp prototype designs within the scope of the present invention have been employed with excellent results in a series of over 80 biliary operations. The cannula and clamp device was incorporated in an assembly of tubing, 4-way stopcock, and two syringes for supply of saline and dye solutions, respectively.

What is claimed is:

1. A cannula and clamp device adapted for operative cystic duct cholangiography comprising (1) a first jaw member with an extended shaft; (2) a second jaw member with an extended shaft which is coextensive and movably connected to said first jaw member wherein the gripping ends of the jaw members in contacting proximity form an annular open-ended cross-section; (3) biasing means for urging said jaw members into contacting proximity; and (4) a cannula which is attached to and inwardy supported by the first jaw member, wherein the injection end of the cannula is rigidly positioned and centered in the annular cross-section formed by the gripping ends of the jaw members, and the feed end of the cannula extends rearwardly and outwardly from the first jaw member; and wherein the jaw members and the extended shafts are angled in a coextensive non-linear configuration.

2. A device in accordance with claim 1 wherein the jaw members and extended shafts are constructed of radiolucent material.

3. A device in accordance with claim 1 wherein the biasing means is a coil spring.

4. A device in accordance with claim 1 wherein the biasing means is an elastomeric spring or band.

5. A device in accordance with claim 1 wherein the biasing means is a screw-adjustable connection between the said jaw members.

6. A device in accordance with claim 1 wherein the annular open-ended cross-section formed by the gripping ends of the jaw members in contacting proximity is circular.

7. A device in accordance with claim 1 wherein the gripping ends of the jaw members are matching incomplete semi-circles relative to the open-ended cross-section.

8. A device in accordance with claim 1 wherein the gripping ends of the jaw members are non-matching arcs which close in an overlapping configuration relative to the open-ended cross section.

9. A device in accordance with claim 1 wherein the gripping ends of the jaw members close in an overlapping teeth configuration relative to the open-ended cross-section.

10. A device in accordance with claim 1 wherein the injection end of the cannula is centered in the annular cross-section and extends beyond the gripping ends of the jaw members.

11. A device in accordance with claim 1 wherein the injection end of the cannula has an open or closed blunt tip, and has liquid-discharge side perforations distributed near the blunt tip.

12. A device in accordance with claim 1 wherein the cannula body is longitudinally rigid and laterally flexible.

* * * * *